United States Patent [19]

Sibley et al.

[11] Patent Number: 5,225,055

[45] Date of Patent: Jul. 6, 1993

[54] METHOD OF CLEANING AND DISINFECTING CONTACT LENSES

[75] Inventors: Murray J. Sibley, Westerville, Ohio; Henry C. Oksman, Mamaroneck, N.Y.

[73] Assignee: Abbott Laboratories, Abbott Park, Ill.

[21] Appl. No.: 743,963

[22] Filed: Aug. 12, 1991

Related U.S. Application Data

[62] Division of Ser. No. 478,107, Feb. 9, 1990, abandoned.

[51] Int. Cl.$^5$ .................................................. C25F 1/00
[52] U.S. Cl. .................................. 204/131; 204/130; 424/616; 514/840; 422/22
[58] Field of Search .............. 424/616; 514/840; 204/131, 130; 422/22

[56] References Cited

U.S. PATENT DOCUMENTS

| | | | |
|---|---|---|---|
| 3,912,451 | 10/1975 | Gaglia, Jr. | 422/30 |
| 4,202,740 | 5/1980 | Stoner et al. | 204/130 |
| 4,414,127 | 11/1983 | Fu | 252/95 |
| 4,473,550 | 9/1984 | Rosenbaum et al. | 424/94.4 |
| 4,518,585 | 5/1985 | Greene et al. | 424/616 |
| 4,521,375 | 6/1985 | Houlsby | 422/29 |
| 4,568,517 | 2/1986 | Kaspar et al. | 422/30 |
| 4,687,997 | 8/1987 | Tao | 324/439 |
| 4,743,447 | 5/1988 | LeRouzic et al. | 424/616 |
| 4,812,173 | 3/1989 | Tsao et al. | 204/128 |
| 4,826,658 | 5/1989 | Kay | 422/30 |
| 4,836,859 | 6/1989 | Konishi et al. | 106/691 |
| 4,839,004 | 6/1989 | Castellini | 252/95 |
| 5,129,999 | 7/1992 | Holland et al. | 204/131 |

FOREIGN PATENT DOCUMENTS 2584503 of 1987 France .
WO89/00430 of 1989 PCT Int'l Appl. .
2094992 of 1982 United Kingdom .

OTHER PUBLICATIONS

McCutcheon's Detergents & Emulsifiers, Allured Publishing Corp., Ridgewood, N.J., 1973, pp. 175–176.

Primary Examiner—Allen J. Robinson
Assistant Examiner—John D. Pak
Attorney, Agent, or Firm—Lonnie R. Drayer; Donald O. Nickey

[57] ABSTRACT

A novel aqueous solution for use in electrochemical cleaning and disinfecting is disclosed. The aqueous solution comprises hydrogen peroxide, a blend of a first ionizable salt and second ionizable salt, and a buffer, with the first ionizable salt being sodium chloride and the second ionizable salt including a metal of Group IA or IIA of the Periodic Table. Preferably a surfactant is included which is a non-ionic surfactant. Also, the preferred buffer is a phosphate buffer system. The preferred second ionizable salt is disclosed as being sodium sulfate.

2 Claims, No Drawings

METHOD OF CLEANING AND DISINFECTING CONTACT LENSES

This is a divisional of application Ser. No. 07/478,107 filed on Feb. 9, 1990, now abandoned.

TECHNICAL FIELD

The present invention relates generally to a cleaning solution, and more particularly, to a contact lens cleaning and disinfecting solution for use in electrochemical cleaning and disinfecting systems.

BACKGROUND ART

Soft contact lenses are generally prepared from certain hydrophilic polymers. The first soft contact lenses marketed were composed of hydroxyethyl methacrylate (HEMA). Today some lenses feature HEMA crosslinked with ethylene glycol dimethacrylate (EDMA), while others are formed of a polymer obtained by polymerizing a mixture of HEMA, EDMA, methacrylic acid and poly (N-vinylpyrrolidone) (PVP). Such lenses exhibit marked hydrophilic properties and when wet are soft and flexible.

While the present invention is useful for both hard and soft contact lenses, the following discussion will focus primarily on the special needs and qualities of soft contact lenses. The primary difference between conventional hard contact lenses and soft lenses is the polar or water attracting character of the hydrophilic gel material from which soft lenses are made. It is this property that gives soft contact lenses their unique physical properties and clinical behavior. This polar or water attracting character of the gel material is caused in part by the presence of hydroxyl groups (—OH) which attract and hold large amounts of water. The high water content of the expanded polymeric matrix results in special difficulties in the cleaning and disinfecting of soft contact lenses. The hydrophilic nature of soft contact lenses makes them especially vulnerable to bacterial contamination.

While studies have demonstrated that bacteria cannot penetrate the intramolecular pores of the hydrophilic polymer, the bacteria have an affinity for the protein and tear deposits on the surfaces of the lens itself. In particular, the compounds and fluid absorbed by the soft lenses provide an excellent bacterial culture media.

Similarly, any residual protein deposits from tear secretions remaining in or on the lens will readily inactivate the most effective germicidal components of a disinfecting system. These organic residues serve as a growth media for a variety of potentially harmful micro-organisms. Thus, in cleaning soft contact lenses, it is important to remove substantially all of the physiological deposits, (i.e. mucins, lipids, and proteins contained in tears and exudates) which are attracted to and build up on the surfaces of the lenses.

In order for soft contact lenses to be effectively cleaned, it is important that all contaminants be removed from both the surfaces and the interior of the lens. Ordinarily, contact lenses are removed each evening and are then reinserted into the eyes upon awakening. The period of removal provides an opportunity to disinfect the lenses by their placement in an antiseptic solution, typically one which contains hydrogen peroxide, although other disinfectants such as chlorhexidine are known and may be used. Hydrogen peroxide permeates a soft contact lens, oxidizes the protein that is present on the surface of the lens and is simultaneously an effective sterilant for any micro-organisms that are present.

The effectiveness of hydrogen peroxide ($H_2O_2$) is well known. However, prolonged exposure to hydrogen peroxide typically causes soft lenses to distort, thereby rendering them unsafe. Furthermore, residual hydrogen peroxide remains following cleaning of the contact lenses and results in eye irritation since hydrogen peroxide is a strong eye irritant. The problem is exacerbated in soft contact lenses, since the hydrogen peroxide can be absorbed into the hydrophilic lens. Thus, when the contact lens is placed on the eye, the hydrogen peroxide is released to irritate and/or harm the sensitive tissues of the conjunctivae or cornea. It is therefore necessary to remove or neutralize any residual hydrogen peroxide both on and in the soft contact lens prior to use.

The instability of hydrogen peroxide solutions is well known as it decomposes into water and oxygen. Allowing a solution of $H_2O_2$ to stand exposed to atmospheric conditions at ambient temperatures will eventually result in complete degradation of the hydrogen peroxide solution. However, the time necessary for complete degradation or neutralization to occur is typically on the order of several days. The prospect of being unable to use the contact lenses for several days presents the user with an intolerable situation.

In the past, when hydrogen peroxide has been utilized in contact lens disinfection regimens, various means have been proposed for the accelerated neutralization or decomposition of residual hydrogen peroxide. For example, it is known in the prior art to neutralize a disinfectant hydrogen peroxide solution through the use of chemical additives. U.S. Pat. No. 4,568,517 to Kaspar et al. discloses a contact lens disinfecting system wherein a chemical neutralizer, e.g. sodium sulfite or sodium thiosulfate is added to the disinfecting solution. U.S. Pat. No. 4,521,375 to Houlsby, teaches a sterilizing treatment with hydrogen peroxide and the neutralization of residual amounts thereof through the use of a chemical neutralizer consisting of sodium pyruvate. However, these methods result in the solution containing and the lenses being left in the presence of undesirable by-products of the chemical neutralization.

An effective solution to the neutralization problem has been found in the use of one or more catalysts to enhance the decomposition of the hydrogen peroxide solution. The use of catalytic agents to accelerate the neutralization of residual hydrogen peroxide absorbed by contact lenses in the course of sterilization is disclosed in U.S. Pat. No. 3,912,451 to Gaglia, Jr. This patent disclosed a method of removing hydrogen peroxide from soft contact lenses through the use of a metallic decomposition catalyst from Group IV-VI of the Period Table. Although Gaglia's method represents an improvement over the prior methods, specifically the ambient decomposition method, in that it substantially shortens the decomposition time, it still takes at least six hours to reduce the percentage of peroxide to an acceptable level for contact lens wear.

Often the catalyst is in the form of an enzyme as disclosed in U.S. Pat. No. 4,473,550 to Rosenbaum et al or in U.S. Pat. No. 4,826,658 to Kay. In both of these patents, the hydrogen peroxide is decomposed by an enzymatic reaction. However, the entire cleaning and disinfecting process disclosed in either patent requires multiple steps, with the wearer of the contact lenses being required to follow relatively specific instructions, which if disregarded could cause physical harm.

Another method for disinfecting contact lenses is disclosed in U.S. Pat. No. 4,202,740 to Stoner et al wherein electrolytically charged chloride ions are used as the disinfectant. In the method of Stoner et al, the device holding the contact lenses must be made of a conductive material in order to serve as a bipolar system whereby the ions flowing through the electrolyte decontaminate the contact lens. However, uneven current distribution throughout the solution will result in shadows and an incomplete disinfection. Further, the voltages must be kept below the potential at which electrolytic oxygen and chloride from the water and sodium chloride are generated.

Electrolysis of hydrogen peroxide as a means to neutralize the disinfectant solution is disclosed in U.S. Pat. No. 4,836,859 to Konishi et al. The aqueous hydrogen peroxide according to that invention contains a single salt such as sodium chloride. The Konishi solution contains a buffer and may even have an antiseptic added. However, the Konishi solution does not include a surfactant, it being well known that hydrogen peroxide is unable to retain its bactericidal properties in the presence of certain surfactants.

Adequate rinsing of the disinfected lenses poses additional problems since it requires a considerable amount of time and personal attention in order to carry out an adequate rinsing procedure. For an adequate soaking and rinsing sequence, it has been found that often four separate rinses are required, which may take a total of 30 minutes or more. Another drawback is the fact that rinsing procedures and sequences are highly subjective and lack reproducibility, such that they can vary widely in effectiveness from one person to another. Furthermore, large volumes of solution are necessary to carry out adequate rinses which over time makes the practice cumbersome and inconvenient. Still further, some rinse systems are confusing to patients, while others are expensive.

It is thus apparent that a need exists for an improved electrolytic cleaning and disinfecting solution which provides easy and effective cleaning and disinfection of contact lenses, particularly soft contact lenses. While the solution of this invention is particularly suited for disinfecting and cleaning of soft contact lenses, it is contemplated herein that the invention would be useful on any article or device that is suited for cleaning and disinfection via electrolysis.

DISCLOSURE OF THE INVENTION

There is disclosed an aqueous solution for use in the electrochemical cleaning and disinfecting of an object in need of cleaning and disinfection, said solution comprising: 1) hydrogen peroxide; 2) a blend of sodium chloride and at least one second ionizable salt, said second ionizable salt including a metal of Group IA or IIA of the Periodic Table; and 3) a buffer.

Preferably the hydrogen peroxide is at a concentration of less than or equal to 3.0%, more preferably in the range of 0.1 to 3.0% and ideally at a concentration about 0.5% by weight. Hydrogen peroxide is commercially available in numerous concentrations and customarily contains a low level of stabilizers. The starting hydrogen peroxide solutions useful in making the solution of this invention will meet the requirements of the United States Pharmacopoeia (USP).

The level of sodium chloride in this invention may range from 0.01 to 2.0% with 0.01 to 1.5% by weight being preferred.

Representative of the second ionizable salts useful in this invention include sodium sulfate, calcium sulfate, potassium bromide, sodium bromide, potassium iodide, sodium iodide and mixtures thereof. The most preferred second ionizable salt is sodium sulfate. The second salt can be at a concentration of from 0.01 to 1.5% by weight.

The buffer is preferably a phosphate buffer system which includes a metal of Group IA or IIA of the Periodic Table, and more preferably comprises at least one of the following: sodium phosphate, sodium monohydrogen phosphate, and sodium dihydrogen phosphate.

There is also disclosed an aqueous solution for use in electrochemical cleaning and disinfecting, said solution comprising:

1) hydrogen peroxide at a concentration of about 0.1 to 3.0% by weight;

2) a blend of sodium chloride and a second ionizable salt, said second ionizable salt including a metal of Group IA or IIA of the Periodic Table;

3) a non-ionic surfactant, said non-ionic surfactant selected from the group of tetra-functional block polymer surfactants terminating in primary hydroxyl groups; and 4) a buffer.

The surfactants useful in this invention are the non-ionic surfactants. These surfactants are a non-ionic tetra-functional series of polyether block-polymers terminating in primary hydroxyl groups. The preferred non-ionic surfactant is Tetronic TM 1107 ®, (BASF Corporation), a tetra-functional block polymer surfactant terminating in primary hydroxyl groups. The Tetronic TM family of surfactants are a series of polyoxyalkylene derivatives of ethylenediamine and are useful in the instant invention. The level of non-ionic surfactant can range from 0.001 to 0.5% by weight.

There is further disclosed an aqueous solution comprising:

1) hydrogen peroxide at a concentration of about 0.5%;

2) a blend of sodium chloride and a second ionizable salt, said sodium chloride being at a concentration of about 0.064%, said second ionizable salt being sodium sulfate at a concentration of about 1.008%;

3) a non-ionic surfactant, said non-ionic surfactant is a tetra-functional block polymer surfactant terminating in primary hydroxyl groups and being at a concentration of about 0.005%; and 4) a phosphate buffer system at a concentration of about 0.3 to 1.0%, said buffer system comprising sodium monohydrogen phosphate and sodium dihydrogen phosphate.

In general the aqueous solution according to this invention contains from 0.1%–3.0% hydrogen peroxide by weight, 0.01%–2.0% of sodium chloride by weight, 0.01%–1.5% of the second ionizable salt by weight, and 0.001%–0.5% of the non-ionic surfactant by weight.

There is also disclosed an aqueous solution for use in the electrochemical cleaning and disinfecting of contact lenses, with the solution comprising hydrogen peroxide of a concentration of about 0.5%, a blend of a first ionizable salt and a second ionizable salt, a non-ionic surfactant which is a tetra-functional block polymer surfactant terminating in primary hydroxyl groups, and a buffer, with the first ionizable salt being sodium chloride and the second ionizable salt including a metal of Group IA or IIA of the Period Table.

One aspect of the present invention provides an aqueous solution for electrochemically cleaning and disinfecting of objects in need of cleaning and disinfection, particularly soft contact lenses, effectively, conveniently, and rapidly.

Another aspect of the invention provides an aqueous solution for the electrochemical disinfection of contact lenses without leaving any undesirable residue of chemical neutralizers or hydrogen peroxide in or on the lenses.

Yet another aspect of the invention resides in an aqueous solution for cleaning and disinfecting contact lenses wherein the lenses may be worn almost immediately after they are cleaned and disinfected without harm or discomfort caused by the neutralized solution.

Other aspects and advantages of the instant invention will be apparent from the following description, examples, and the appended claims.

DETAILED DESCRIPTION OF THE INVENTION

Specifically, the present invention is concerned with a cleaning and disinfecting solution for use in the electrochemical cleaning and disinfecting of contact lenses. The present invention is also concerned with a method for cleaning contact lenses wherein the contact lenses are immersed in a buffered salt solution containing hydrogen peroxide and thereafter, the solution is subjected to electrolysis. While most contact lens solutions currently contain hydrogen peroxide at a concentration of about 3%, it has been discovered that superior results can be achieved by the instant solution which contains about 0.5% hydrogen peroxide by weight. This is somewhat surprising given the commonly accepted wisdom that a 3% $H_2O_2$ solution is required for effective disinfection of contact lenses.

During electrolysis, the solution of this invention has applied through it an electric current which is sufficient to cause the generation of free radicals and neutralization of the hydrogen peroxide. It is important to note that electrolyzed hydrogen peroxide alone does not result in a solution of the proper tonicity for occular use.

The aqueous solution of this invention is intended to be used in an electrolysis device. The device, in general, comprises a container for holding the solution and the objects to be cleaned (lens case), electrodes and electronics for the delivery of current and control of the cleaning/disinfection process. The container can be made of nonconductive materials such as glass, most rigid or semi-rigid plastics, or any other material which is not significantly chemically reactive with hydrogen peroxide or the free radicals generated during the disinfecting/cleaning process. The device may be provided with a cover which can be secured to the container to seal the treatment chamber thereby preventing leakage or spillage of the solution. The covers are provided with openings or vents to permit gases to escape.

Mounted on or near the bottom of the container are two elongated thin wire or foil electrodes comprising an anode and a cathode. Electrically connected to the ends of the anode and cathode, respectively, are a positive conductor and a negative conductor. The electrodes are preferably made of a metal alloy or other conducting material which is not readily oxidized, e.g. platinum, rhodium, iridium, carbon, platinum-rhodium alloy or platinum-iridium alloy. For electrode stability an alloy is the preferred choice as pure elements tend to have weaker bonds and degrade more rapidly under high current densities.

While some of the suitable materials for the electrodes may also have a catalytic effect on neutralizing the peroxide solution when used in sufficient quantity as taught by Gaglia, the size of the electrodes, used in this invention is typically about 5.0 mm in width by 20 mm in length, is such as to make the amount of electrode material much less than the catalytic amount needed for any material increase in the decomposition of the peroxide by catalytic action. Absent the electrolysis process taught herein, the insertion of the electrodes in the sterilizing solution would provide no material advantage over merely allowing the peroxide to normally decompose under ambient conditions.

Also mounted on the bottom of the container or attached to the cover is a cage, on which or in which the lenses are placed so that the lenses are surrounded on all sides by the instant solution.

A source of electrical potential which serves as a power supply provides the energy for rapid decomposition and neutralization of the solution. The source may be A.C. or D.C. In a preferred embodiment the electrical source is a conventional storage battery or transformer with a D.C. potential of between 1.5 and 20 volts, which is high enough to generate free radicals. A power source capable of generating square waves having peaks of sufficient amplitude to generate free radicals and neutralize the solution is alternatively preferred. A timing and control unit is provided for carrying out the process. The construction and operation of the timing and control unit is well within the skill of the artisan.

In general, the timing and control unit governs three process time periods. During the first period, the lenses are placed in the solution as previously described. During this first period, the solution according to this invention, removes contaminants from the lenses and kills infectious microorganisms. During the second time period, electric current is applied to the solution. The current is at a level in the range of about 5 to 300 milliamperes, sufficient to cause the generation of free radicals as well as a pH change. The electrical current disinfects by pH changes as well as free radical formation and also neutralizes any residual hydrogen peroxide, thereby leaving a weak salt solution having a tonicity near the tonicity of the natural fluids surrounding the eyes. The first few seconds following the current interruption are includes in the second period. It is during this time that the free radicals dissipate and the pH returns to the physiologic range. The third time period follows the interruption of the electrolysis current. It is during the third time period that the cleaned, and sterilized lenses may be removed from the device and placed directly in the eye.

In use, the container of the device is first partially filled with a solution according to this invention. When the contact lens wearer retires to bed or at any other time when it is desired to clean and sterilize the lenses, the lenses are placed in the solution (in the container or cage which is part of the electrolysis device) and left there a sufficient time for cleaning, sterilization and neutralization to be achieved.

The resultant solution (after electrolysis) is dilute saline having a tonicity and pH like that of human tears. Thus, the solution that is absorbed into or remains on the surface of the contact lenses causes no discomfort to the wearer after insertion into the eyes.

It is to be appreciated that the foregoing is a description of one embodiment of a device the instant solution can be used in. However, variations and modifications of the device can be made without departing form the spirit and scope of the invention. Moreover, the invention is not limited to sterilizing contact lenses and may apply to the disinfection of any article or object which can be cleaned and sterilized by electrolysis.

The presence of only sodium chloride and hydrogen peroxide in the solution results in the generation of sodium and chloride ions upon electrolysis, with the sodium ions reacting to form sodium hydroxide at a concentration that is too alkaline for toleration by ocular tissue. Further, the presence of chloride ions in very high concentration results in a solution which will be damaging to the eye. On the other hand, the presence of sodium sulfate by itself results, following electrolysis, in a pH which is too acidic, with the problem being exacerbated when an ordinary surfactant is added to the solution. However, it has been discovered that a blend of sodium chloride and a second ionizable salt permits the sodium hydroxide formed as a consequence of the ionization of the sodium chloride to be balanced by the products formed as a consequence of the ionization of the second salt. Thus the pH of the fully electrolyzed solution is compatible with ocular tissue. Following electrolysis, tonicity or osmolarity of the solution of this invention is approximately 260 milliosmols per 1000 gms of solution, such that the solution is isotonic with respect to fluids associated with the eye.

The use of hydrogen peroxide disinfects the lens and renders it free of any living pathogenic organisms which could cause eye infection. However, to optimize the usefulness of the liquid solution of this invention, it is desirable that is provide cleaning for the lenses so as to remove physiological deposits of mucins, lipids, and/or proteins which are attracted to and build up on the lens. Thus, it is desirable that a surfactant be included in the aqueous formulation.

There are four major types of surfactants known: anionic, cationic, amphoteric, and non-ionic. It has been discovered that non-ionic surfactants are the preferred choice for use in this invention for two reasons. First, non-ionic surfactants tend to have the least affect on the pH of a system, and second, non-ionic surfactant are the least likely type of surfactants to become polarized when the solution in which they are contained undergoes electrolysis.

More specifically, it has been discovered that non-ionic surfactants of tetra-functional block-polymer type terminating in primary hydroxy groups are preferable, with the most preferred non-ionic surfactant being Tetronic TM 1107, (a product of BASF Corp.) Surprisingly it was discovered that the addition of a non-ionic surfactant will dramatically alter the final pH of the solution following electrolysis. Thus, the choice of surfactant is critical.

The aqueous solution according to the present invention also preferably contains a buffer system. Preferably the buffer system is a phosphate buffer system which includes a metal of Group IA or IIA of the Periodic Table with the more preferred buffer system comprising at least one of the following: sodium phosphate, sodium mono-hydrogen phosphate, and sodium dihydrogen phosphate. In some cases a borate buffer could be substituted for the phosphate buffer.

As a consequence of choosing the various components for the liquid solution of this invention the pH, both before and after electrolysis, is about 7.0 + or − 0.5. Furthermore, it can be appreciated that this pH is acceptable for exposure to contact lenses and ocular tissue.

BEST MODE FOR CARRYING OUT THE INVENTION

In actual use, a pair of contact lenses may be thoroughly cleaned and disinfected by their placement into about three (3) ml. of the solution of this invention, with that solution then being electrolyzed.

A representative formula for the liquid solution of the invention is set forth in Table I below.

TABLE I

DX-130 Solution

| Ingredient | Concentration by Weight |
|---|---|
| 1. Hydrogen peroxide | 0.5% |
| 2. Sodium chloride | 0.064% |
| 3. Sodium sulfate | 1.008% |
| 4. Tetronic 1107 (surfactant) | 0.005% |
| 5. Sodium phosphate (dibasic) buffer | 0.67% |
| 6. Sodium phosphate (monobasic) buffer | quantity sufficient to pH a of 7.0 |
| 7. Water | |

The solution according to this invention can be prepared in any convenient manner as the order of addition is not critical. Thus, a standard $H_2O_2$ solution can have added to it the salts, surfactant and buffer system with distilled or de-ionized water being added to arrive at the proper dilution. For purposes of further discussion the formulation of Table I will hereinafter be referred to as the DX-130 Solution. Also, the electrolysis device used in the following Examples and as described supra, will be referred to as the DX-130 Device.

The invention will be better understood in view of the following examples, which are illustrative only and should not be construed as limiting the invention.

EXPERIMENTAL—DETERMINATION OF SOLUTION COMPOSITION

Example 1—Control

To 10.0 ml. of a 3% hydrogen peroxide solution was added 0.1 mg. of sodium chloride. The pH of the solution was 4.0. Following electrolysis via the DX-130 Device for 2 hours with 6 volts DC impressed across platinum/iridium electrodes, the solution exhibited a pH of 10.5 which is far too alkaline.

Example 2—Control

The procedure of Example 1 was repeated, except that 1.0 mg. of sodium sulfate was substituted for the sodium chloride. Following electrolysis, the solution exhibited a pH of 6.0, which is not alkaline enough.

Example 3—Control

The procedure of Example 2 was repeated, except that 0.1 mg. of a non-ionic surfactant, Tween®-20 (polysorbate-20, sold by ICI Industries) was added to the solution prior to electrolysis. Without electrolysis, it was observed that the addition of the non-ionic surfactant to a solution of hydrogen peroxide did not appreciably alter the pH of the solution. However, following electrolysis, the solution exhibited a pH of 3.0, which is far too acidic.

Example 4—Invention

The procedure of Example 1 was repeated except that 0.1 mg. of sodium chloride and 1.0 mg. of sodium sulfate were used. Following electrolysis the solution exhibited a pH of 7.5, and a tonicity of 1.0% (sodium chloride equivalent) both of which are acceptable for use around eye tissue.

Example 5-Invention

It was discovered that effective disinfection could be obtained at lower hydrogen peroxide concentration than is commonly associated with contact lens cleaning solutions which contain hydrogen peroxide. Optimum disinfection with respect to the safety of the contact lenses and the wearer's eyes, was obtained when a solution of 100 ml 0.5% hydrogen peroxide to which was added 64 mg. of sodium chloride and 1008 mg. of sodium sulfate was subjected to electrolysis.

Example 6—Control

The procedure of Example 5 was repeated with 0.05% of the non-ionic surfactant Pluronic ® (sold by BASF Corporation) being added to the solution prior to electrolysis. Following electrolysis, the solution exhibited a pH of 4.0%, which is far too acidic.

Example 7—Invention

The procedure of Example 6 was repeated except that 0.05% of Tetronic TM 1007 was substituted as the non-ionic surfactant. Following electrolysis, the solution exhibited a tonicity of 1.0 sodium chloride equivalent and a pH of 6.8.

Example 8—Invention

The procedure of Example 7 was repeated with two buffer systems. The first was a borate buffer system comprising boric acid (0.01%) and sodium borate (0.1%), the second was a phosphate buffer system comprising sodium phosphate (dibasic, 0.275%) and sodium phosphate (monobasic, 0.099%). Following electrolysis of the two solutions, the solution with a borate buffer system exhibited a tonicity of 1.0 (sodium chloride equivalent) and a pH of 9.0, while the solution with a phosphate buffer system exhibited a tonicity of 1.0 (sodium chloride equivalent) and a pH of 6.8. Thus the phosphate buffered solution was found to be extremely effective.

Example 9—Testing of DX-130 Solution

This study was designed to determine the efficacy of the DX-130 Solution against viable bacteria and fungi by measuring the reduction of the challenge organisms over time when exposed to the solution according to this invention.

The Challenge Organisms were:
a. *Staphylococcus epidermidis* ATCC 17917.
b. *Pseudomonas aeruginosa* ATCC 15442.
c. *Serratia marcescens* ATCC 14041.
d. *Candida albicans* ATCC 10231.
e. *Aspergillus fumigatus* ATCC 10894

The Media and reagents used were:
a. Sterile saline blanks.
b. Sterile Phosphate Buffered Saline (PBS).
c. PBS with 0.05% Tween 80 (PBS+)

The recovery media were:
1) Sabouraud Dextrose Agar plates (SDA).
2) Trypticase Soya Agar plates (TSA).

Preparation of Challenge Microorganisms

The bacteria were subcultured on TSA through three daily transfers, incubating at 35°±2° C. On the test day, the cells were washed from the agar surface with PBS, centrifuged for 15 minutes. The pellets resuspended in fresh PBS and diluted to give approximately $10^8$ cfu/ml by spectrophotometric methods. The adjusted suspension was centrifuged as above and the pellet resuspended in an equal volume of organic soil.

The *Candida albicans* was subcultured on SDA through two daily transfers and allowed to incubate at 35°±2° C. for two days prior to the day of the test. On the test day, cells were washed from the agar surface with PBS+ and treated in the same manner as the bacteria.

The *Aspergillus fumigatus* was subcultured onto SDA and incubated to 20°-25° C. for five days. The hyphae were washed from the surface with PBS+, macerated and certrifuged at 2000 rpm for 15 minutes. The pellet was resuspended in PBS+ and serially diluted in saline blanks. Appropriate dilutions were plated in duplicate onto SDA plates and incubated at 20-25 for 2-3 days. The plates were counted, the cfu/ml calculated and the suspension adjusted to give approximately $10^8$ cfu/ml. The spore suspension was stored at 4°±2° C. for no more than thirty days. Prior to testing the suspension was centrifuged as above and the pellet resuspended in an equal volume of organic soil.

Each challenge microorganism was tested apart from each other microorganism in each test solution. One tenth milliliter of each standardized inoculum was added to 9.9 ml of DX-130 Solution in a DX-130 unit. The unit was turned on and samples were withdrawn at 5, 10, 20, 30, 60 minutes and at the end of cycle.

At "0" time the microorganism were assayed using PBS instead of the test solution. This established the zero time control.

The zero time control was assayed at the end of the cycle to ensure the organism count was stable during the time of the test.

The D-Value was calculated using the Stumbo method (Stumbo, C. R., Food Technology, 1948, pp228-240). The results are shown in the following table.

TABLE II

When tested as described the following D-Values were achieved:

| Organism | D-Value |
| --- | --- |
| *Candida albicans* | 5.0 minutes |
| *Aspergillus fumigatus* | 26.5 minutes |
| *Serratia marcescens* | 3.2 minutes |
| *Pseudomonas aeruginosa* | 1.0 minutes |
| *Staphylococcus epidermidis* | 1.7 minutes |

This data demonstrates that the solution of this invention, when used in conjunction with an electrolysis device, is a very effective disinfectant.

Example 10

Anti-Microbial Efficacy Using Bacteria and Fungi

This test was designed to indicate the disinfectant efficacy of the chemical disinfection system (device and solution) for Class III contact lens care. The test simulates consumer use and consists of cleaning, soaking, and rinsing twenty lenses and their appropriate controls inoculated with viable microorganisms in organic soil as recommended in the U.S. Food and Drug Administration's 1985 Guidelines. Any tests lens or soaking solution producing growth of a challenge organism after processing constitutes failure of the lens to be disinfected by the disinfection system.

The contact lenses used in this study were:
a. Soflens Contact Lenses
b. Durasoft 3 Contact Lenses
c. Softmate B Contact Lenses
d. Permaflex Naturals Contact Lenses The Materials used in this study were:
1. Organic soil—heat inactivated bovine serum containing $10^8$ heat killed cells of *Saccharomyces cerevisiae*/ml.

The Challenge Organisms acquired from ATCC were:
a. *Staphylococcus epidermidis*, ATCC 19717
b. *Pseudomonas aeruginosa*, ATCC 15442
c. *Serratia marcescens*, ATCC 14041
d. *Candida albicans*, ATCC 10231
e. *Aspergillus fumigatus*, ATCC 10894

The Media and Reagents used were:
A. Recovery broth
b. Sabouraud Dextrose Agar plates (SDA)
c. Trypticase Soya Agar plates (TSA)
d. Sterile Saline Blanks
e. Sterile Phosphate Buffered Saline (PBS)
f. PBS with 0.05% Tween 80 (PBS+)
g. Environmental Control Plates Bacteria were subcultured on TSA through daily transfers and incubated at $30°\pm2°$ C. in ambient air. On the fourth day, the cells were washed from the agar surface with PBS and centrifuged at 2000 rpm for 15 minutes. The pellets were resuspended in fresh PBS, and diluted to give approximately $10^8$ cfu/ml. The adjusted suspensions were centrifuged as above and the pellet resuspended in an equal volume of organic soil.

The yeast was subcultured on SDA through daily transfers and incubated at $30°\pm2°$ C. in ambient air. The inoculum was prepared from a two day culture and prepared in the same manner as the bacteria but substituting PBS+ for PBS.

The fungus was subcultured onto SDA and incubated at $20°-25°$ C. for five days. The hyphae were washed from the surface with PBS+, macerated, filtered and centrifuged at 2000 rpm for 15 minutes. The pellet was resuspended in PBS+ and serially diluted in saline blanks. Appropriate dilutions were plated in duplicate onto SDA plates and steaked out.

The plates were counted, the cfu/ml calculated, the spore suspension adjusted to $10^8$ cfu/ml and stored at $4°\pm2°$ C. until use (did not exceed 30 days). The suspension was resuspended in OS prior to the test.

Sets of five lenses were aseptically transferred from their storage container to a sterile Petri dish. The negative and positive control lenses were placed individually in separate dishes. Each side of each lens was inoculated with 0.01 ml of lens inoculum. The negative control lens was inoculated with 0.01 ml of organic soil on each side. The positive control lens was inoculated with 0.01 ml of inoculum on each side. All lenses were allowed to dry seven minutes before beginning the lens care procedure.

Technical personnel wore sterile gloves when processing each lens.

Each inoculated lens was cleaned by placing three drops of DX-130 Solution on each surface of each lens and rubbed for 20 seconds.

The lens was rinsed thoroughly in a steady stream of the same solution for 10 to 20 seconds until the lens was clear and placed in the basket of the DX-130 Device.

The cases were filled with DX-130 solution and the device plugged in.

At the end of the cycle, the lenses were removed from their baskets and transferred to their respective tubes of recovery broth. The corresponding lens soaking solutions were transferred to their marked tubes of recovery broth. The control lenses and their soaking solution were processed in the same manner, but the positive control was processed in a separate area.

The filamentous fungal media were incubated at $24°-31°$ C. and observed for growth at fourteen days. The yeast and bacterial media were incubated at $35°2°$ C. in ambient air and observed for growth at fourteen days.

The test solutions fulfill the pass criteria if there are no challenge organisms isolated from the lens or fluid cultures; there was growth of the challenge organism in the positive control cultures.

When tested as described, the DX-130 Solution disinfected the four groups of Class III Contact Lenses when challenged with the five organisms specified.

Example 11

Anti-viral Efficacy Using *Herpes simplex*

This test procedure was designed to determine the disinfectant efficacy of a regimen for Class III contact lens care. The test simulated consumer use and consists of cleaning, soaking and rinsing test lenses and the appropriate controls previously inoculated with viable *Herpes simplex* virus in an organic soil. Any test lens producing virus-specific cytopathogenic effects (CPE) after processing constitutes failure of the lens disinfection system.
a. Soflens (polymacon) contact lenses.
b. Durasoft 3 contact lenses.
c. Softmate B contact lenses.
d. Permaflex Naturals contact lenses.

General materials and supplies used were:
1. *Herpes simplex* I, ATCC VR260 (HSVI). The virus was previously titered and stored at $-80°$ C.
2. African Green Monkey Kidney Cells, ATCC CCL-81 (VERO), confluent monolayer cultures maintained at $37°\pm1°$ C. in a $5\pm1\%$ $CO_2$ in air atmosphere.
3. Medium 199 with Earle's salts supplemented with heat inactivated calf bovine serum (CBS), glutamine, and Penicillin-Streptomycin (M199).
4. Sterile Phosphate Buffered Saline (PBS).
5. Organic soil—CBS containing approximately $10^8$ heatkilled cells of *Saccharomyces cerevisiae*, ATCC 9763, per ml. Prepared and stored at $-80°$ C. prior to use.

The virus stock culture was titered and adjusted to contain approximately $10^6$ $CCID_{50}$/ml (50% cell culture infectious doses per milliliter) and stored frozen in liquid nitrogen. The virus stock was thawed, diluted 10-fold in M199 through $10^{-8}$ and one-ml aliquots of appropriate dilutions were plated onto confluent Vero monolayers. The cells were incubated at $37°\pm1°$ C. in 51% $CO_2$, for 30 minutes to allow the virus to adsorb to the cells. After adsorption, the media was withdrawn from the monolayers, the cells were washed once with PBS and refed with fresh M199.

The monolayers were incubated for five days at 37°±1° C. in 5±1% $CO_2$ and subsequently observed for virus-specific cytopathogenic effects (CPE).

Equal amounts of HSV and organic soil were mixed together and applied to the 20 test lenses by dispensing 0.01 ml on each side of each lens.

Groups of five lenses were processed together and allowed to sit at ambient conditions for approximately three to seven minutes in a sterile Petri dish before processing.

Three drops of DX-130 solution were placed on each side of the lens located in the palm of a sterile gloved hand. The lens was rubbed between the forefinger of the other hand and palm until the lens appeared clean.

The lens was rinsed thoroughly with DX-130 Solution until the lens appeared clean. The lens was transferred to its appropriate lens basket using a sterile forceps. The cleaned, rinsed lenses (two per basket) were placed in the DX-130 unit filled with DX-130 cleaning and disinfecting solution and the unit was plugged into an electrical outlet. This procedure was repeated for all twenty test lenses.

At the end of the cycle, each lens, in turn, was placed in 1 ml of CBS and incubated at 37°±1° C. in 5±1% $CO_2$ in air atmosphere for 30 minutes.

Following the 30 minute incubation in CBS the lenses were removed, applied to a VERO monolayer for viral adsorption and incubated at 37°±1° C. in 5±1% $CO_2$ in air atmosphere for thirty minutes. Following the adsorption period, the lenses were removed, the monolayers washed with 1 ml of PBS, refed M199 and incubated at 37°±1° C. in 5±1% $CO_2$ in air atmosphere for five days.

Fluid remaining in each respective lens case was collected, diluted 1:1 with M-199 and a 2.0 ml aliquot applied to a VERO monolayer and incubated at 37°±1° C. in 5±1% $CO_2$ in air atmosphere for 30 minutes. Following the adsorption period, the fluid was removed, the monolayer washed with 1 ml of PBS, refed M199 and incubated at 37°±1° C. in 5±1% $CO_2$ in air atmosphere for five days.

Two uninoculated lenses were passed through the entire cleaning-disinfecting procedure to detect toxicity imparted to the lenses by the procedure. They were processed in the same manner as the test lenses.

Two uninoculated, untreated lenses were placed directly on the VERO monolayer and processed in the same manner as the test lenses to detect inherent toxicity in the lenses.

One inoculated lens was processed with sterile PBS at ambient temperature for the same time period and in the same manner as the test lenses. Another inoculated lens was taken directly from the Petri dish to the lens basket without cleaning or rinsing, this served as a viability control.

The test is considered a success only if no CPE is observed in any of the test lenses and their soaking solution cultures and CPE can be demonstrated from positive controls.

RESULTS

See Tables III, IV, and V for Day 5 observations.

When tested as described, the DX-130 Solution disinfects each of the four groups of Class III contact lenses when challenged with *Herpes simplex* ATCC VR260.

TABLE III

| DILUTION | STOCK TITER | INOCULUM TITER |
|---|---|---|
| $10^{-3}$ | + + + + | + + + + |
| $10^{-4}$ | + + + + | + + + + |
| $10^{-5}$ | + + + + | + + + + |
| $10^{-6}$ | + + − + | + − − − |
| $10^{-7}$ | − − − − | − − − − |
| $CCID_{50}/ml^* =$ | $2.1 \times 10^6$ | $4.7 \times 10^5$ |

TABLE IV

| DX-130 Disinfection Solution Class III Lenses | | |
|---|---|---|
| LENS NUMBER | LENS RESULTS | FLUID RESULTS |
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |
| 11 | − | − |
| 12 | − | − |
| 13 | − | − |
| 14 | − | − |
| 15 | − | − |
| 16 | − | − |
| 17 | − | − |
| 18 | − | − |
| 19 | − | − |
| 20 | − | − |

* = 50% Cell Culture Infective Dose per Milliliter Reed and Muench, American Journal of Hygience, 1938.
Lens ID = 1–5 (B&L Soflens), 6–10 (W&J Durasoft), 11–15 (B-H Softmate B), 16–20 (Coopervision Permaflex).
− = No CPE observed
+ = CPE Observed

TABLE V

| Controls | | |
|---|---|---|
| B&L Soflens | Lens | Fluid |
| C1 | 0 | 0 |
| C2 | 0 | 0 |
| C3 | 0 | na |
| C4 | 0 | na |
| C5 | − | − |
| C6 | + | + |
| Wesley Jessen Durasoft 3 | Lens | Fluid |
| C1 | 0 | 0 |
| C2 | 0 | 0 |
| C3 | 0 | na |
| C4 | 0 | na |
| C5 | − | − |
| C6 | + | + |
| Barnes-Hind Softmate B | Lens | Fluid |
| C1 | 0 | 0 |
| C2 | 0 | 0 |
| C3 | 0 | na |
| C4 | 0 | na |
| C5 | − | − |
| C6 | + | + |
| Coopervision Permaflex | Lens | Fluid |
| C1 | 0 | 0 |
| C2 | 0 | 0 |
| C3 | 0 | na |
| C4 | 0 | na |
| C5 | − | − |

TABLE V-continued

| | Controls | |
|---|---|---|
| C6 | + | + |

- = No CPE observed
+ = CPE observed
0 = No cytotoxicity observed
na = Not applicable The results from this experiment demonstrate that the solution of this invention, when used in an electrolysis device, is effective in the disinfection of contact lenses. Not only does the solution of this invention provide excellent disinfecting properties, but also results in a lens that can be directly inserted into the eye due to the resulting solution's tonicity and pH subsequent to electrolysis. While the aqueous solution herein described constitutes a preferred embodiment of this invention, it is to be understood that the invention is not limited to this precise formulation and that changes may be made therein without departing from the scope of the invention which is defined in the appended claims.

What is claimed is:

1. A method of cleaning and disinfecting contact lenses comprising the steps of: (a) placing contact lenses in an aqueous solution having a pH in the range of 6.5-7.5; and (b) subjecting the solution to electrolysis for a time adequate to clean and disinfect the lenses with the aqueous solution having a pH in the range of 6.5-7.5 after being subject to electrolysis, the aqueous solution comprising:
   (a) 0.1%-3.0% by weight hydrogen peroxide;
   (b) 0.01%-2.0% by weight sodium chloride;
   (c) 0.01%-1.5% by weight of at least one second ionizable salt selected from the group consisting of sodium sulfate, calcium sulfate, potassium bromide, sodium bromide, potassium iodide and sodium iodide;
   (d) 0.001%-0.5% by weight of a non-ionic surfactant selected from the group consisting of tetra-functional block polymer surfactants terminating in primary hydroxyl groups; and
   (e) a phosphate buffer system at a concentration of about 0.3%-1.1% by weight.

2. A method of cleaning and disinfecting contact lenses according to claim 1 wherein the hydrogen peroxide is at a concentration of about 0.5% by weight, the sodium chloride is at a concentration of abut 0.64% by weight, the second ionizable salt is sodium sulfate at a concentration of about 1.008% by weight, and the phosphate buffer system is at a concentration of about 0.8% by weight and comprises sodium monohydrogen phosphate and sodium dihydrogen phosphate.

* * * * *

UNITED STATES PATENT AND TRADEMARK OFFICE
CERTIFICATE OF CORRECTION

PATENT NO. : 5,225,055
DATED : July 6, 1993
INVENTOR(S) : Murray J. Sibley, et. al.

It is certified that error appears in the above-indentified patent and that said Letters Patent is hereby corrected as shown below:

On the Title page, item [73] add the names of the following inventors:
Gerald Wilhelm Hietala
Joseph Zehavi Eisner Column 6, line 51, "includes" should be --included--

Column 12, line 15, "35°2°" should be --35° ± 2° --.

Signed and Sealed this

Twenty-second Day of February, 1994

Attest:

BRUCE LEHMAN

Attesting Officer

Commissioner of Patents and Trademarks